March 12, 1963 E. S. BOERNER Plant Pat. 2,237
ROSE PLANT
Filed May 21, 1962
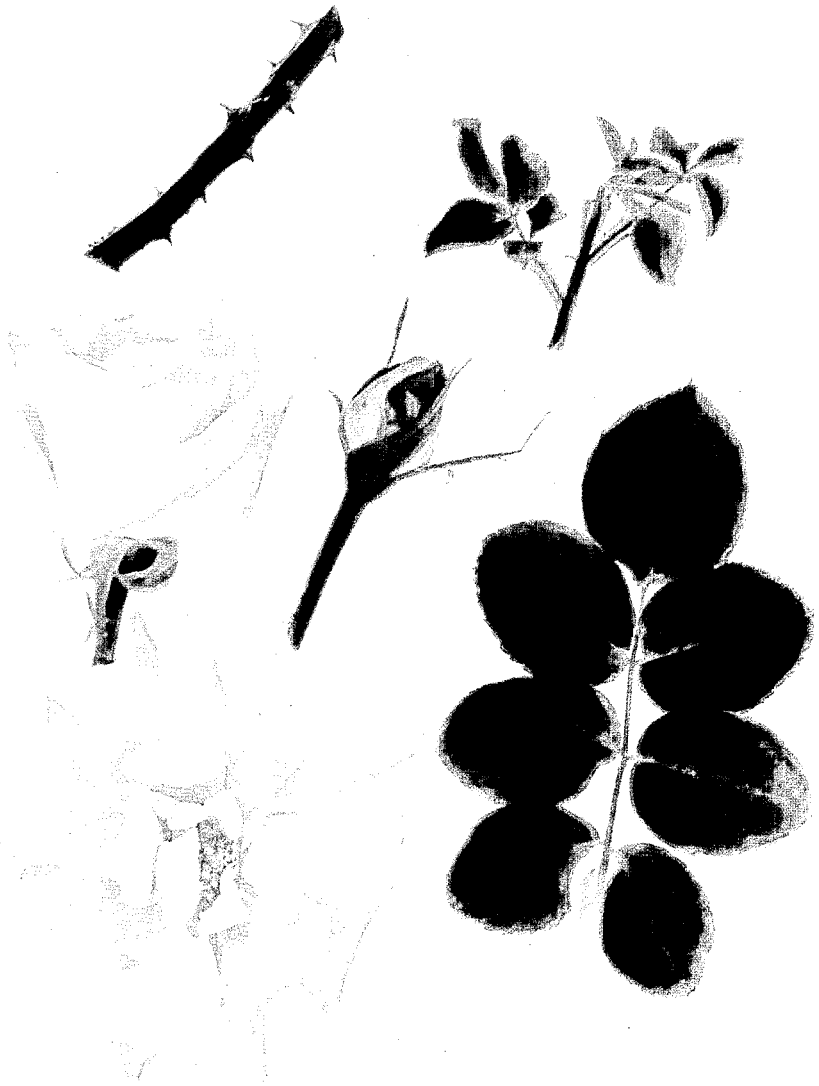
Inventor.
E. S. Boerner
By: Robb & Robb
Attorneys.

United States Patent Office

Plant Pat. 2,237
Patented Mar. 12, 1963

2,237
ROSE PLANT

Eugene S. Boerner, Newark, N.Y., assignor to Jackson & Perkins Company, Newark, N.Y., a corporation of New York Filed May 21, 1962, Ser. No. 196,538
1 Claim. (Cl. 47—61)

The present invention relates to a new and distinct variety of rose plant of the hybrid tea class, which was originated by me by crossing an unnamed and unpatented seedling of "Rome Glory" (Plant Patent No. 304) with the variety "Golden Masterpiece" (Plant Patent No. 1,284).

The primary objective of this breeding was to produce a new rose variety of the hybrid tea type in which there are combined the characteristics of a tall habit of growth, large and fragrant flowers. This objective was fully achieved, along with other desirable features, as evidenced by the following unique combination of characteristics which are outstanding in the new variety and which distinguish it from its parents, as well as from all other varieties of which I am aware:

(1) A tall and vigorous habit of plant growth;

(2) Large, high-centered flowers;

(3) A distinctive and attractive general color tonality of the flowers corresponding to Rose Red, lightly overcast with Tyrian Rose, with the lower half of the petals lightly overcast with Apricot Yellow; and (4) A strong Old Rose perfume fragrance of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Rome Glory."

*Pollen parent.*—"Golden Masterpiece."

Classification:

*Botanic.*—Hybrid tea.

*Commercial.*—Hybrid tea.

*Flower*

(Observations made from specimens grown outdoors at Newark, New York, in the late morning during the early part of the month of September.)

Blooming habit: Recurrent—continuous.

Bud:

*Size.*—Medium.

*Form.*—Ovoid; it is not affected by wet or hot weather.

*Color.*—When sepals first divide—Bordeaux, Plate 12. When petals begin to unfurl—Eugenia Red, Plate 13. When half-blown: inside of petals—Rose Red, Plate 12, very lightly overcast with Begonia Rose, Plate 1; reverse of petals—Light Orange Yellow, Plate 3, with upper half of petals lightly overcast with Old Rose, Plate 13.

*Sepals.*—Slightly branched; curl back when petals begin to unfurl. Color: inside—Pale Olivine, Plate 32; outside—Bice Green, Plate 17.

*Calyx.*—Color—Bice Green, Plate 17. Shape—apple. Size — long. Aspect — smooth. Odor when rubbed—none.

*Peduncle.* — Length — medium. Aspect — rough. Strength—erect; slender. Color—Absinthe Green, Plate 31.

*Opening.*—Opens up well; it is not affected by adverse weather conditions.

Bloom:

*Size.*—Large. Average size when fully expanded—from 5½ inches to 6 inches.

*Borne.*—Both singly and several together.

*Stems.*—Medium length; strong.

*Form (when first open)*—High-centered. Permanence—retains its form to the end, but outer petals curl back.

*Petalage.*—Double (full but open center). Number of petals under normal conditions—from 45 to 50.

*Color.*—Center of flower—Rose Red, Plate 12, lightly overcast with Tyrian Rose, Plate 12. Outer petals—Rose Red, Plate 12, very lightly overcast with Rose Color, Plate 12. Base of petals (aiglet)—Empire Yellow, Plate 4. Inside of petals—Rose Red, Plate 12, very lightly overcast with Tyrian Rose, Plate 12, and with lower half of petals lightly overcast with Apricot Yellow, Plate 4. Reverse of petals—Cream Color, Plate 16, with upper half of petals lightly overcast with Rose Pink, Plate 12, and with lower half of petals overcast with Buff Yellow, Plate 4. General tonality from a distance—Rose Red, Plate 12, very lightly overcast with Tyrian Rose, Plate 12.

*Discoloration.*—General tonality at end of first day—Rose Red, Plate 12, very lightly overcast with Tyrian Rose, Plate 12. Second day—Rose Red, Plate 12, lightly overcast with Tyrian Rose, Plate 12. Third day—Rose Red, Plate 12, lightly overcast with Tyrian Rose, Plate 12.

Petals:

*Texture*—Leathery; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Strong. Nature—"Old Rose perfume" (centifolia).

*Lasting quality.*—On the plant—long. As cut flower—long.

*Genital Organs*

Stamens, anthers: Medium size; many; regularly arranged around styles. Color—Light Cadmium, Plate 4.

Stamens, filaments (threads): Medium length. Color—Scarlet, Plate 1.

Pollen: Color—Maize Yellow, Plate 4.

Styles: Bunched; uneven length; short; thin.

Stigmas: Color—Naples Yellow, Plate 16.

Ovaries: All enclosed in calyx.

Hips: None.

Seeds: None.

*Plant*

Form: Bush.

Growth: Vigorous; upright.

Foliage: Compound of 5–7 leaflets.

*Size.*—Medium.

*Quantity.*—Normal.

*Color.*—New foliage: Upper side—Oil Green, Plate 5, with edges overcast with Carmine, Plate 1;

under side—Light Yellowish Olive, Plate 30. Old foliage: upper side—Varley's Green, Plate 18; under side—Light Cress Green, Plate 31.

*Shape.*—Oval.

*Texture.*—Upper side—glossy. Under side—smooth.

*Ribs and veins.*—Ordinary.

*Edge.*—Serrated (saw-toothed).

*Serration.*—Single; small.

*Leaf stem.*—Color—Glass Green, Plate 31. Under side—prickly.

*Stipules.*—Short; smooth.

Wood:

*New wood.*—Color—Absinthe Green, Plate 31, lightly overcast with Van Dyke Red, Plate 13. Bark—smooth.

*Old wood.*—Color—Biscay Green, Plate 17. Bark—smooth.

Thorns:

*Thorns.*—Quantity: on main stalks from base—ordinary; on laterals from stalk—ordinary. Form—

Narrow base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a tall and vigorous habit of plant growth, large and high-centered flowers, a distinctive and attractive general color tonality of the flowers corresponding to Rose Red, lightly overcast with Tyrian Rose, and with the lower half of the petals lightly overcast with Apricot Yellow, and a strong "Old Rose perfume" flower fragrance.

No references cited.